United States Patent
Carls et al.

(10) Patent No.: US 8,231,661 B2
(45) Date of Patent: Jul. 31, 2012

(54) SYSTEMS AND METHODS FOR MINIMALLY INVASIVE FACET FUSION

(75) Inventors: Thomas A. Carls, Memphis, TN (US); Newton H. Metcalf, Jr., Memphis, TN (US)

(73) Assignee: Warsaw Orthopedic, Warsaw, IN (US)

( * ) Notice: Subject to any disclaimer, the term of this patent is extended or adjusted under 35 U.S.C. 154(b) by 293 days.

(21) Appl. No.: 12/570,264

(22) Filed: Sep. 30, 2009

(65) Prior Publication Data

US 2011/0077685 A1   Mar. 31, 2011

(51) Int. Cl.
*A61B 17/88* (2006.01)
*A61B 17/70* (2006.01)

(52) U.S. Cl. .................. 606/279; 606/247; 606/104

(58) Field of Classification Search .......... 606/246–247, 606/279, 86 A, 98–99, 104
See application file for complete search history.

(56) References Cited

U.S. PATENT DOCUMENTS

| | | | |
|---|---|---|---|
| 5,242,444 A * | 9/1993 | MacMillan | 606/86 R |
| 6,966,930 B2 * | 11/2005 | Arnin et al. | 623/17.11 |
| 2004/0254575 A1 * | 12/2004 | Obenchain et al. | 606/61 |
| 2005/0049705 A1 * | 3/2005 | Hale et al. | 623/17.11 |
| 2005/0131438 A1 | 6/2005 | Cohn | |
| 2005/0159746 A1 * | 7/2005 | Grob et al. | 606/61 |
| 2006/0079908 A1 | 4/2006 | Lieberman | |
| 2006/0084977 A1 | 4/2006 | Lieberman | |
| 2006/0265076 A1 | 11/2006 | Carter et al. | |
| 2007/0250166 A1 | 10/2007 | McKay | |
| 2007/0270825 A1 | 11/2007 | Carls et al. | |
| 2008/0161810 A1 * | 7/2008 | Melkent | 606/79 |
| 2009/0131986 A1 | 5/2009 | Lee et al. | |

OTHER PUBLICATIONS

International Search Report and Written Opinion for U.S. Application PCT/US2010/050715 mailed on Apr. 11, 2011.

* cited by examiner

*Primary Examiner* — Eduardo C Robert
*Assistant Examiner* — Jacqueline Johanas

(57) ABSTRACT

Apparatus and methods for facet fusion include an insertion tool and a guide tool coupled to one another. The insertion tool has a proximal end portion and an opposite distal end portion. The distal end portion of the insertion tool is configured to retain an interbody implant, such as, for example, an inter-facet implant configured for placement between a superior facet and inferior facet of a facet joint. The proximal end portion of the insertion tool includes a handle. The guide tool includes an elongated body with a passage extending between and opening at its distal and proximal ends. A linking member extends between and adjustably connects the guide tool to the insertion tool so that the passage of the guide tool is alignable with the interbody implant retained on the insertion tool while the insertion tool and guide tool are in substantially orthogonal relation to one another.

15 Claims, 3 Drawing Sheets

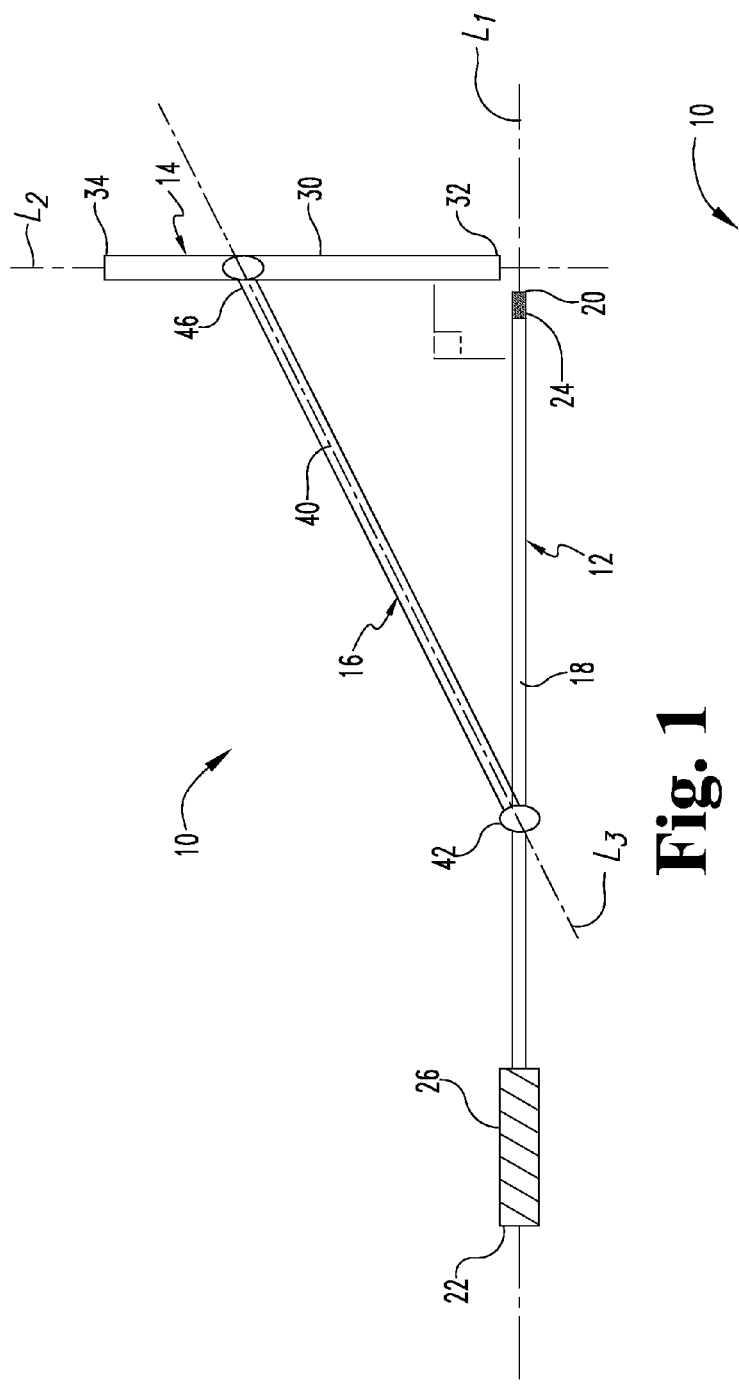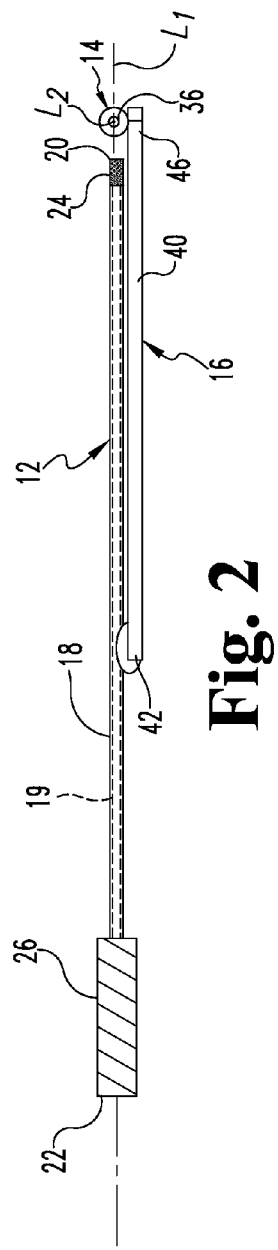

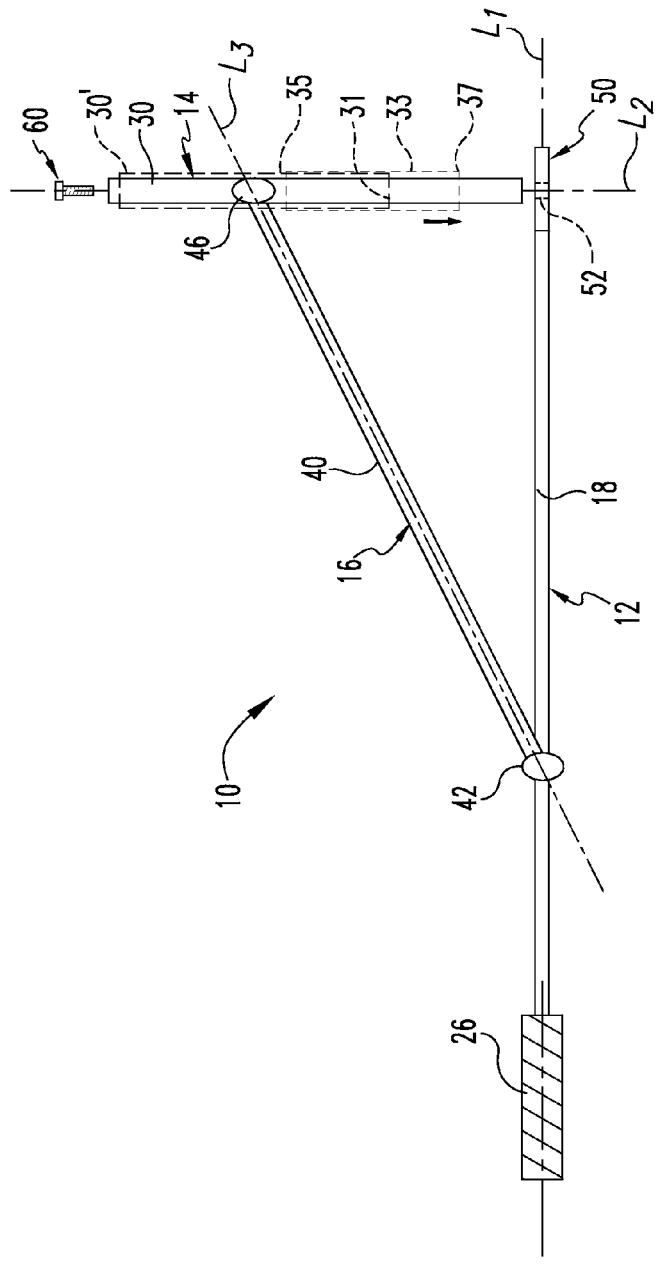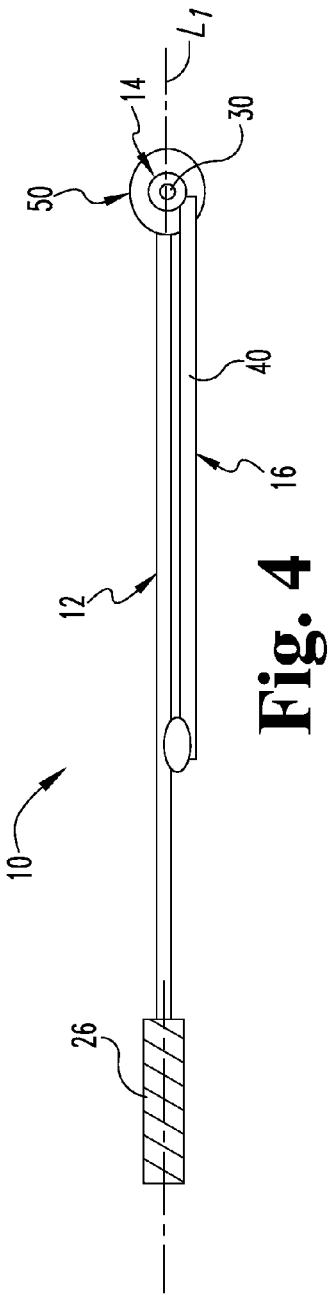

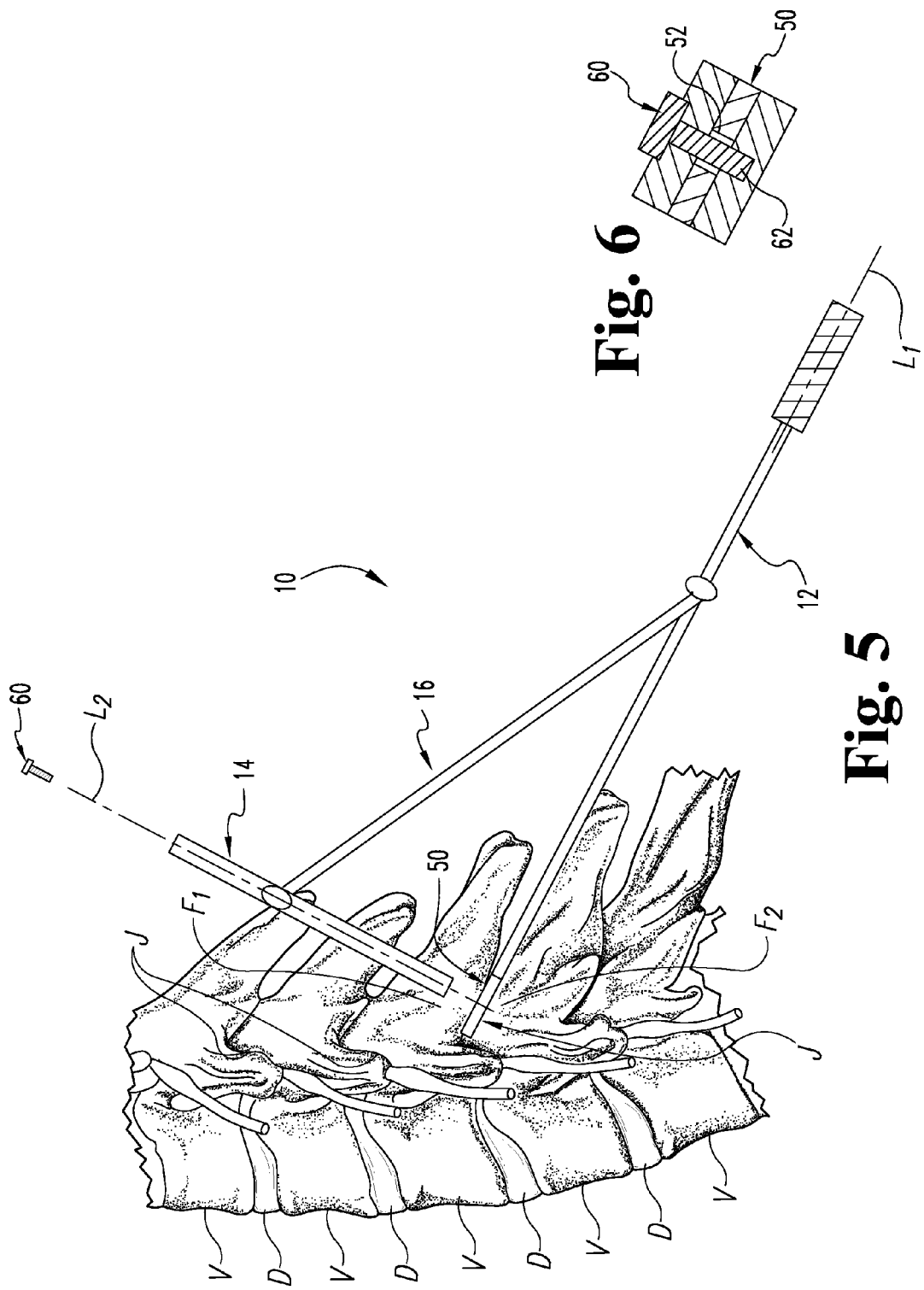

SYSTEMS AND METHODS FOR MINIMALLY INVASIVE FACET FUSION

BACKGROUND

The invention relates generally to medical devices and procedures. More particularly, the invention relates to apparatus and methods for minimally invasive instrumentation and implants for spinal fusion.

Bone fixation devices, such as, for example, bone screws, interbody implants, staples, pins, wires and/or clamping mechanisms, can be used in various medical procedures. For example, known bone screws can be used to repair fractured bone tissue by securing adjacent portions of the bone tissue together to stabilize and/or limit the movement of bone tissue. Known interbody implants can be used between adjacent portions of bone tissue to provide support for and to facilitate bone growth between the portions of bone tissue. For example, some known bone screws and interbody implants can be used as a part of a spinal fixation procedure.

In some procedures, for example, a facet screw can be inserted across the facet joint of the spinal column to fix and/or limit the motion of the facet joint. Such known procedures can include, for example, translaminar facet screw fixation, which includes inserting a facet screw from the base of the spinous process on the contralateral side and through the lamina to traverse the facet joint in a plane perpendicular to the joint surfaces. Facet screws can also be inserted using a transfacet approach, which involves inserting a bone screw via a midline incision or an ipsilateral incision. Other procedures involve positioning an implant in the facet joint. Such known procedures, however, often involve the use of multiple tools and/or multiple steps, and are performed in an open incision in which the facet joint is exposed and tissue retracted sufficiently to allow placement of the screw through the facet, or placement of the interbody implant between the portions of the facet, under direct vision. Since placement of the facet screw and the implant are accomplished from two different approaches to the facet, procedures that employ facet screw fixation and implant placement into the facet joint involve retraction of sufficient tissue around the facet to open the incision to simultaneously expose both approaches for use by the surgeon.

Thus, a need exists for improved insertion tools, implants, and procedures for insertion and securement of implants at locations within a patient's body that can minimize intrusion into tissue along the approach to and around the implantation location.

SUMMARY

Apparatus and methods for fusion of a joint are described herein. In some embodiments, the apparatus includes an insertion tool and a guide tool coupled to one another. The insertion tool has a proximal end portion and a distal end portion. The distal end portion of the insertion tool is configured to retain an implant, such as, for example, an implant configured for placement between a superior facet and inferior facet of a facet joint. The proximal end portion of the insertion tool includes a handle. The guide tool includes an elongated body with a passage extending between its distal and proximal ends. A linking member extends between and adjustably connects the guide tool to the insertion tool so that the passage of the guide tool aligns with the interbody implant retained on the insertion tool. The apparatus and method can be employed in minimally invasive surgical techniques for placement of the implant in the facet joint and an anchor into the facet joint. Applications in non-minimally invasive procedures are also contemplated.

According to a further aspect, an apparatus includes an insertion tool with a proximal end portion and a distal end portion opposite the proximal end portion. The distal end portion of the insertion tool includes an implant engaging portion configured to retain an inter-facet implant on the insertion tool. The insertion tool further includes a shaft extending from the implant engaging portion along a first longitudinal axis to the proximal end portion. The apparatus also includes a guide tool with an elongated body defining a passage extending between a distal end and a proximal end. The elongated body extends along a second longitudinal axis between the distal and proximal ends. The apparatus also includes a linking member coupled to the shaft of the insertion tool and to the elongated body of the guide tool. The linking member adjustably connects the guide tool and the insertion tool to one another with the first longitudinal axis in substantially orthogonal relation to the first longitudinal axis and with the distal end of the guide tool on the second longitudinal axis spaced proximally away from the first longitudinal axis of the insertion tool.

According to another aspect, an apparatus comprises an insertion tool including an elongate shaft extending along a first longitudinal axis between a proximal handle portion and a distal implant engaging portion that is opposite the proximal handle portion. The apparatus also includes an inter-facet implant engaged to the implant engaging portion extending distally from the insertion tool along the first longitudinal axis. The apparatus also includes a linking member with a first end coupled to the shaft of the insertion tool that extends from the first end in an oblique orientation to the shaft of the insertion tool to a second end opposite the first end. The apparatus also includes a guide tool coupled to the second end of the linking member for guiding an anchor to the inter-facet implant. The guide tool includes an elongate body extending along a second longitudinal axis between a proximal end and a distal end. The linking member is coupled to the elongate body between the distal and proximal ends of the elongate body in an oblique orientation to the elongate body. The elongate body also defines a passage that extends along a second longitudinal axis. The second longitudinal axis is substantially orthogonal to the first longitudinal axis and the second longitudinal axis intersects the inter-facet implant.

According to yet another aspect, a method comprises: inserting through a first opening in a patient a distal end portion of an insertion tool that includes an implant mounted to the distal end portion of the insertion tool; positioning the implant between a superior facet and inferior facet of a facet joint; inserting through a second opening in a patient a distal end portion of a guide tool to a location adjacent one of the superior facet and the inferior facet; and guiding a bone anchor along the guide tool through the one of the superior facet and inferior facet, through the implant, and into the other of the superior facet and the inferior facet.

These and other aspects are also discussed below.

BRIEF DESCRIPTION OF THE DRAWINGS

FIG. 1 is an elevation view of a surgical instrument apparatus for minimally invasive insertion of an implant and anchor from separate approaches to the same implantation location.

FIG. 2 is a top view of the apparatus of FIG. 1.

FIG. 3 is an elevation view of the apparatus of FIG. 1 with an implant coupled thereto.

FIG. 4 is a top view of the apparatus and implant of FIG. 3.

FIG. 5 is an elevation view of a spinal column segment with the surgical instrument apparatus of FIG. 1 employed to position the implant in a facet joint of the spinal column segment from a first approach and to guide a bone anchor through the implant from a second approach.

FIG. 6 is a sectional, diagrammatic view of the facet joint with the implant positioned therein and an anchor through the implant engaged to the superior and inferior facets.

DETAILED DESCRIPTION

For the purposes of promoting an understanding of the principles of the invention, reference will now be made to the embodiments illustrated in the drawings and specific language will be used to describe the same. It will nevertheless be understood that no limitation on the scope of the invention is intended. Any alterations and further modifications in the illustrated devices and described methods and further applications of the principles of the invention as disclosed herein are contemplated as would normally occur to one skilled in the art to which the invention relates.

Apparatus and methods for inserting implants between adjacent bone portions of the spinal column are described herein. In some embodiments, the apparatus includes an insertion tool having a first shaft extending between a proximal handle and a distal implant engaging portion, and a guide tool adjustably mounted to the insertion tool so that the guide tool extends transversely to the insertion tool. The guide tool includes a passage extending between distal and proximal ends of the guide tool so that the passage is in alignment with an implant engaged to the implant engaging portion of the insertion tool. An inter-facet implant can be engaged to the insertion tool for insertion between a superior facet and an inferior facet of a facet joint. When the implant is in the desired positioned, a bone anchor can be guided with the guide tool and then through one of the facets, through the inter-facet implant, and into the other facet to secure the facets and implant to one another.

In some embodiments, a method includes inserting percutaneously or through a small incision a distal end portion of an insertion tool that includes an inter-facet implant engaged thereto and positioning the inter-facet implant between a superior facet and an inferior facet of a facet joint. The insertion tool also includes a guide tool adjustably coupled thereto, and the guide tool is adjusted to align it with the inter-facet implant. A bone anchor is guided by the guide tool and through the inter-facet implant to secure the facets and inter-facet implant to one another. In one specific embodiment, the bone anchor is guided through the implant along an approach that is substantially orthogonal to the approach along which the implant is positioned in the facet joint In some embodiments, a method includes inserting an inter-facet implant between a superior and inferior facet of a facet joint from a first approach to the facet joint; referencing a position of a guide to the location of the inter-facet implant; and guiding a bone anchor into the facet joint and through the inter-facet implant from a second approach that is substantially orthogonal to the first approach to the facet joint so that the bone anchor extends through the facet implant and is engaged to at least one of the superior and inferior facets. In one specific embodiment, the first and second approaches are formed by separate stab incisions or holes into the patient that form separate minimally invasive surgically approaches to the facet joint separated from one another by the skin and tissue of the patient. The apparatus and method allows placement of inter-facet implants and bone anchors through the inter-facet implant without requiring exposure of the facet joint to accommodate placement of both the inter-facet implant and the bone anchor or requiring the procedure to be performed under direct vision by the surgeon.

In some embodiments, a kit includes an inter-facet implant, a bone anchor positionable through the inter-facet implant, and an insertion and guide apparatus. The insertion and guide apparatus includes an insertion tool removably engageable to the inter-facet implant and a guide tool adjustably connected to the insertion tool so that a position of the guide tool is referenced to the inter-facet implant when the inter-facet implant is engaged to the insertion tool. With the inter-facet implant engaged to the insertion tool, the guide tool can guide the bone anchor through the inter-facet implant from an approach that is substantially orthogonal to the approach along which the insertion tool extends. In one specific embodiment, the guide tool includes an elongated passage extending between distal and proximal ends of the guide tool that lies along the approach from which the bone anchor is inserted.

Referring to FIGS. 1-4, there is shown an apparatus 10 that includes an insertion tool 12 and a guide tool 14 adjustably connected to one another with a linking member 16. Insertion tool 12 includes an elongated shaft 18 extending along a longitudinal axis L1 between a distal end 20 and a proximal end 22. Distal end 20 includes an implant engaging portion 24 that is configured to removably engage an implant 50, as discussed further below. Proximal end 22 includes a handle 26 that facilitates manipulation of insertion tool 12 into the patient. In one embodiment, at least a portion of handle 26 and/or shaft 18 is operably linked to implant engaging portion 24 so that the operator can manipulate implant engaging portion 24 to grip or release an implant. Shaft 18 includes a sufficient length along longitudinal axis L1 so that when the implant 50 is positioned at the desired location in the patient, handle 26 is located outside the patient or is otherwise readily accessible by the surgeon to manipulate the implant engaged to insertion tool 12.

Various configurations for implant engaging portion 24 are contemplated. In one embodiment, implant engaging portion 24 is a threaded tip extending from an inner shaft 19 (FIG. 2) that extends through or along shaft 18 to a knob or other engagement structure formed by handle 26. The knob is rotated to rotate the inner shaft and the threaded tip to engage implant engaging portion 24 with the implant 50. In other embodiments, implant engaging portion 24 can include two or more arms that grip the implant between the arms. In yet other embodiments, implant engaging portion 24 includes two or more arms that are expanded or moved outwardly to grip the implant. In other embodiments, the implant is frictionally or adhesively engaged to implant engaging portion 24. Still other embodiments contemplate any suitable arrangement for removably retaining an implant to insertion tool 12.

Guide tool 14 includes an elongated body 30 that extends between a distal end 32 and a proximal end 34. Elongated body 30 extends along a longitudinal axis L2 that is substantially orthogonal to longitudinal axis L1 of insertion tool 12. In one embodiment, longitudinal axis L2 is orthogonal to longitudinal axis L1 to provide precise alignment of guide tool 14 with the implant 50 engaged to insertion tool 12. As shown in FIG. 2, longitudinal axis L2 of guide tool 14 intersects longitudinal axis L1 of insertion tool 12 so that the location of a bone anchor 60 guided with guide tool 14 relative to the implant 50 engaged to insertion tool 12 is precisely known to the surgeon. Other embodiments contemplate that longitudinal axis L2 is offset from longitudinal axis L1 by a known distance.

Body 30 includes a passage 36 extending between and opening at distal and proximal ends 32, 34. In the illustrated embodiment, passage 36 is completely enclosed by body 30. Other embodiments contemplate that passage 36 is partially enclosed by body 30. In yet other embodiments, passage 36 is defined by a rail or other structure extending along body 30. Passage 36 lies on or extends along longitudinal axis L2 so that an anchor 60 guided along passage 30 of guide tool 14 is advanced to a location referenced to longitudinal axis L1 of insertion tool 12. In the illustrated embodiment, longitudinal axis L1 and longitudinal axis L2 intersect one another so that the anchor 60 guided with guide tool 14 will extend through the implant engaged to insertion tool 12 on longitudinal axis L1. Other embodiments contemplate arrangements where longitudinal axis L2 is offset from longitudinal axis L1, so long as the insertion path of the bone anchor 60 positioned with guide tool 14 is referenced to the position of the implant 50 engaged to insertion tool 12.

Apparatus 10 also includes link member 16 with an elongated arm 40 that extends between and adjustably connects insertion tool 12 to guide tool 14. Elongated arm 40 includes a first end 42 pivotally connected to shaft 18 of insertion tool 12 with a hinge or other suitable coupling arrangement. Elongated arm 40 extends from first end 42 to a second end 46 adjustably connected to guide tool 14. In a first orientation of link member 16, longitudinal axis L1 and longitudinal axis L2 are orthogonal to one another and intersect one another and arm 40 extends along a longitudinal axis L3 that is obliquely oriented to longitudinal axes L1 and L2. The hinged connections at first end 42 and second end 46 allow the orientation of longitudinal axes L1 and L2 to vary slightly from orthogonal to accommodate the patient anatomy. It is further contemplated that one or both of the connections at first and second ends 42, 46 can be adjusted distally and proximally along the respective shaft 18 or body 30 and then re-secured in the adjusted position to facilitate alignment of axes L1 and L2.

In another embodiment, body 30 of guide tool 14 includes two or more telescoping portions that allow the length of body 30 to be adjusted to accommodate the patient anatomy. For example, FIG. 3 shows an alternative arrangement of body 30' with a proximal portion 35 having an intermediate end 31, and a distal portion 33 around proximal portion 35 shown in phantom. Distal portion 33 is shown retracted proximally relative to intermediate end 31 of proximal portion 35. Distal portion 33 can be advanced distally along longitudinal axis L2 and into the opening formed in the patient so that the length of body 30' of the guide member is adjustable to position distal end 37 of distal portion 33 at a position more adjacent implant engaging portion 24.

FIGS. 3 and 4 show inter-facet implant 50 engaged to implant engaging portion 24 of insertion tool 12 and extending distally from insertion tool 12 along longitudinal axis L1. Guide tool 14 is aligned with implant 50 so that passage 36 directs bone anchor 60 along longitudinal axis L2 to a desired location relative to implant 50. In one embodiment, implant 50 includes a hole 52 extending between upper and lower surfaces of implant 50, and passage 50 is aligned with hole 52. Longitudinal axis L2 is aligned with hole 52 so that bone anchor 60 is guided through hole 52 of implant 50.

FIG. 5 shows apparatus 10 in position relative to a portion of a spinal column segment, and FIG. 6 shows implant 50 and bone anchor 60 engaged to a facet joint. Spinal column segment includes a number of vertebrae V, with adjacent one of vertebrae V separated by a respective one of spinal discs D. Facet joints J are located between respective ones of adjacent vertebrae V. Facet joints J each include a superior facet F1 and an inferior facet F2. It is contemplated that the spinal column segment is part of a patient in which spinal surgery is to be performed with the present invention. It is also contemplated that the spinal column segment may comprise a non-human or non-living animal substrate, such as may be present with a training model to teach methods employing the surgical instruments and implants discussed herein.

Implant 50 is positioned between facets F1, F2 with insertion instrument 12 along a first approach that generally parallels longitudinal axis L1. Guide tool 14 is positioned along a second approach that generally parallels longitudinal axis L2 and is substantially orthogonal to longitudinal axis L1. Bone anchor 60 is guided by guide tool 14 and includes a bone engaging portion 62 that extends through superior facet F1, implant 50 and into inferior facet F2 to form the final construct, as shown in FIG. 6.

In FIGS. 5 and 6, for the sake of clarity, the skin and surrounding tissue of the patient's body is not depicted. It should be appreciated that insertion tool 12 and implant 50 can be inserted to facet joint J through a first minimally invasive insertion path through the skin and tissue that is sized to accommodate implant 50 but not other portions of apparatus 10. Guide tool 14 is insertion through a separate, second minimally invasive insertion path through the skin and tissue that is formed by or defined by guide tool 14. In one embodiment, guide tool 14 is a guided to superior facet F1 along a guide wire or dilator to the target location. A hole can be formed in facet F1, or other bone preparation can be completed, through guide 14 to accommodate engagement of the bone anchor 60. In one embodiment, bone anchor 60 is a bone screw with a threaded shaft 62 that threadingly engages one or all of inferior facet F2, implant 50 and superior facet F1. Other embodiments contemplate other configurations for bone anchor 60, including partially threaded shafts 62, non-threaded shafts 62, and expandable shafts 62, for example.

Prior to insertion of implant 50, the facet joint J can be prepared by removing, scraping, forming or cutting bone material to form an implant insertion location between facets F1 and F2. Although the apparatus 10 is shown in FIG. 5 as being inserted via a substantially midline incision, in other embodiments, the apparatus 10 can be inserted via an incision lateral to the spinous process SP (e.g., an ipsilateral incision or a contralateral incision). In some embodiments, the implant 50 and bone anchor 60 can be inserted percutaneously through separate incisions. For example, in some embodiments, the implant 50 and bone anchor 60 can each be inserted in a minimally-invasive manner through separate incisions that each has a size less than 15 mm.

In some embodiments, the method optionally includes coupling the implant 50 to a distal end portion of insertion tool 12 while the distal end portion of the insertion tool 12 is outside of the patient's body. Bone anchor 60 can be coupled to the distal end of a driver (not shown) while bone anchor 60 is outside the patient. The implant 50 is inserted into the facet joint J, and the driver is inserted through or along guide tool 14. In some embodiments, for example, the bone anchor 60 can be removably coupled to the distal end portion of the driver tool by a retention member, a snap ring, a magnetic coupling, an adhesive coupling or the like.

A passageway is defined within the tissue while guide tool 14 is disposed within the patient's body. In some embodiments, the passageway can be defined using the guide tool 14, which is inserted under fluoroscopic guidance or other suitable viewing system. In other embodiments, the passageway is defined by a separate retractor, tube, sleeve or other device to accommodate guide tool 14 and/or anchor 60.

Moreover, in some embodiments, the passageway for insertion of implant 50 can be defined by the insertion tool 12 by advancing implant 50 and insertion tool 12 through the tissue under fluoroscopic guidance or other suitable viewing system. In other embodiments, the passageway is defined by a separate retractor, tube, sleeve or other device to accommodate insertion tool 12 and/or implant 50 into the patient to facet joint J.

Although various embodiments have been described as having particular features and/or combinations of components, other embodiments are possible having a combination of any features and/or components from any of embodiments as discussed above. As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the terms "proximal" and "distal" refer to the direction closer to and away from, respectively, an operator (e.g., surgeon, physician, nurse, technician, etc.) who would insert the medical implant and/or instruments into the patient. For example, the portion of a medical instrument first inserted inside the patient's body would be the distal portion, while the opposite portion of the medical device (e.g., the portion of the medical device closest to the operator) would be the proximal portion.

While the application has been illustrated and described in detail in the drawings and foregoing description, the same is to be considered as illustrative and not restrictive in character, it being understood that only the selected embodiments have been shown and described and that all changes, modifications and equivalents that come within the spirit of the invention as defined herein or by any of the following claims are desired to be protected.

What is claimed is:

1. A method, comprising:
   inserting through a first opening in a patient a distal end portion of an insertion tool that includes a solid implant mounted to the distal end portion of the insertion tool, coupling the solid implant to the distal end portion of the insertion tool while the distal end portion of the insertion tool is outside of the patient's body;
   positioning the solid implant between a superior facet and inferior facet of a facet joint; inserting through a second opening in a patient a distal end portion of a guide tool to a location adjacent one of the superior facet and the inferior facet; and
   guiding a bone anchor along the guide tool through the one of the superior facet and inferior facet, through the solid implant, and into the other of the superior facet and the inferior facet.

2. The method of claim 1, wherein the first opening and the second opening are separate percutaneous openings.

3. The method of claim 1, wherein the first opening and the second opening are separate stab incisions.

4. The method of claim 1, wherein the bone anchor is a threaded bone anchor that threadingly engages at least one of the superior facet and the inferior facet.

5. The method of claim 1, wherein inserting the distal end portion of the guide tool includes advancing a distal portion of the guide tool into the second opening while moving the distal portion of the guide tool relative to a proximal portion of the guide tool.

6. The method of claim 1, further comprising: adjusting an orientation of the guide tool relative to the insertion tool with a linking member that extends from the insertion tool to the guide tool, wherein the linking member extends outside the patient from the first opening to the second opening.

7. The method of claim 1, further comprising: preparing an implant insertion location between the superior facet and the inferior facet.

8. The method of claim 1 further comprising: inserting a driver through the guide tool and engaging the driver with the bone anchor for guiding the bone anchor.

9. The method of claim 8 wherein the bone anchor is removably coupled to a distal end portion of the driver.

10. A method, comprising:
    inserting through a first opening in a patient from a first approach a distal end portion of an insertion tool that includes a solid inter-facet implant mounted to the distal end portion of the insertion tool, coupling the solid inter-facet implant to the distal end portion of the insertion tool while the distal end portion of the insertion tool is outside of the patient's body;
    positioning the solid inter-facet implant between a superior facet and inferior facet of a facet joint; inserting through a second opening in a patient a distal end portion of a guide tool to a location adjacent one of the superior facet and the inferior facet; and
    guiding a bone anchor along the guide tool from a second approach that is substantially orthogonal to the first approach through the one of the superior facet and inferior facet, through the solid inter-facet implant, and into the other of the superior facet and the inferior facet.

11. The method of claim 10, wherein the first approach and the second approach are formed by separate stab incisions.

12. The method of claim 10, further comprising: preparing an implant insertion location between the superior facet and the inferior facet.

13. A method, comprising:
    inserting an insertion tool through a first opening in a patient, the insertion tool having a solid inter-facet implant engaged thereto, coupling the solid inter-facet implant to the distal end portion of the insertion tool while the distal end portion of the insertion tool is outside of the patient's body;
    positioning the solid inter-facet implant between a superior facet and an inferior facet of a facet joint;
    inserting a guide tool through a second opening in a patient, the guide tool being adjustably coupled to the insertion tool for alignment with the solid inter-facet implant; and
    guiding a bone anchor along the guide tool and through the solid inter-facet implant to secure the superior facet, inferior facet and the solid inter-facet implant to one another.

14. The method of claim 13, wherein the bone anchor is guided through the implant along an approach that is substantially orthogonal to the approach along which the implant is positioned in the facet joint.

15. The method of claim 13, further comprising: preparing an implant insertion location between the superior facet and the inferior facet.

* * * * *